US012485285B2

(12) United States Patent
Smith

(10) Patent No.: US 12,485,285 B2
(45) **Date of Patent: *Dec. 2, 2025**

(54) INDIVIDUALIZED ADAPTATION OF MEDICAL PROSTHESIS SETTINGS

(71) Applicant: Cochlear Limited, Macquarie University (AU)

(72) Inventor: Zachary Mark Smith, Greenwood Village, CO (US)

(73) Assignee: Cochlear Limited, Macquarie University (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/483,794

(22) Filed: Oct. 10, 2023

(65) Prior Publication Data

US 2024/0108902 A1 Apr. 4, 2024

Related U.S. Application Data

(63) Continuation of application No. 17/261,775, filed as application No. PCT/IB2019/056066 on Jul. 16, 2019, now Pat. No. 11,813,460.

(Continued)

(51) Int. Cl.

| | |
|---|---|
| ***A61N 1/36*** | (2006.01) |
| ***A61N 1/05*** | (2006.01) |
| ***H04R 25/00*** | (2006.01) |

(52) U.S. Cl.

CPC ....... *A61N 1/36146* (2013.01); *A61N 1/0541* (2013.01); *A61N 1/36038* (2017.08); *H04R 25/70* (2013.01); *A61N 1/36171* (2013.01)

(58) Field of Classification Search

CPC .............. A61N 1/36146; A61N 1/0541; A61N 1/36038; A61N 1/36171; A61N 1/0534; A61N 1/362; A61N 1/372; H04R 25/70

See application file for complete search history.

(56) References Cited

U.S. PATENT DOCUMENTS

| | | | |
|---|---|---|---|
| 6,068,652 | A | 5/2000 | Cohen et al. |
| 7,889,879 | B2 | 2/2011 | Dillon et al. |

(Continued)

FOREIGN PATENT DOCUMENTS

| | | | |
|---|---|---|---|
| KR | 10-1617474 | B1 | 5/2016 |
| WO | 2018005583 | A1 | 1/2018 |

OTHER PUBLICATIONS

Fitzgerald, M.B., et al., "Feasibility of real-time selection of frequency tables in an acoustic simulation of a cochlear implant," Ear Hear. vol. 34(6), pp. 763-772 (2013).

(Continued)

*Primary Examiner* — Catherine M Voorhees

(74) *Attorney, Agent, or Firm* — Edell, Shapiro & Finnan, LLC

(57) ABSTRACT

Presented herein are techniques for adapting/transitioning operation of a medical prosthesis, such as an auditory prosthesis, from a first or initial group of settings to a second or target group of settings. The adaptation in the operation of the medical prosthesis from the first group of settings to the second group of settings occurs over a period of time and in a series of individualized (recipient-specific) incremental steps. That is, the adaptation process occurs in incremental steps that are set based on attributes/characteristics of the recipient of the specific medical prosthesis so that the adaptation is made as unobtrusive to the recipient as possible.

20 Claims, 10 Drawing Sheets

Related U.S. Application Data

(60) Provisional application No. 62/703,100, filed on Jul. 25, 2018.

(56) References Cited

U.S. PATENT DOCUMENTS

| | | | | |
|---|---|---|---|---|
| 7,908,012 | B2 | 3/2011 | Svirsky | |
| 8,401,656 | B2 | 3/2013 | Smoorenburg | |
| 8,774,432 | B2 | 7/2014 | Förhlich et al. | |
| 9,067,069 | B2 | 6/2015 | Svirsky | |
| 9,838,804 | B2 * | 12/2017 | Bernardi | G06F 18/2185 |
| 11,813,460 | B2 * | 11/2023 | Smith | A61N 1/36038 |
| 2009/0043359 | A1 * | 2/2009 | Smoorenburg | A61N 1/36039 607/57 |
| 2009/0157143 | A1 | 6/2009 | Edler et al. | |
| 2011/0264165 | A1 | 10/2011 | Molnar et al. | |
| 2016/0066107 | A1 | 3/2016 | Recker | |
| 2017/0224992 | A1 * | 8/2017 | Kulkarni | A61N 1/37241 |
| 2017/0359661 | A1 * | 12/2017 | Goorevich | H04R 25/70 |
| 2018/0085581 | A1 | 3/2018 | Fung et al. | |

OTHER PUBLICATIONS

Fitzgerald, M.B., et al., "Self-Selection of Frequency Tables with Bilateral Mismatches in an Acoustic Simulation of a Cochlear Implant," J Am Acad Audiol. , vol. 28(5): pp. 385-394 (May 2017).

Fu, Q.J., et al., "Perceptual learning following changes in the frequency-to-electrode assignment with the Nucleus-22 cochlear implant," Journal of the Acoustical Society of America, vol. 112,(4) pp. 1664-1674 (2002).

Greenwood , D.D., "A cochlear frequency-position function for several species-29 years later," The Journal of the Acoustical Society of America, vol. 87(6), pp. 2592-2605 (1990).

Greenwood , D.D., "Critical Bandwidth and the Frequency Coordinates of the Basilar Membrane," The Journal of the Acoustical Society of America, vol. 33, pp. 1344-1356 (1961).

Jethanamest, D., et al., "A New Software Tool to Optimize Frequency Table Selection for Cochlear Implants," Otol Neurotol., vol. 31(8): pp. 1242-1247 (11 pages) (Oct. 2010).

Jethanamest, D., et al., "A Smartphone Application for Customized Frequency Table Selection in Cochlear Implants," · Otol Neurotol., vol. 38(8): pp. e253-e261 (Sep. 2017).

Smalt, C.J., et al., "Neural adaptation and perceptual learning using a portable real-time cochlear implant simulator in natural environments," Conf Proc IEEE Eng Med Biol Soc. (33rd) pp. 1145-1148 (2011).

Svirsky, M.A., et al., "Gradual adaptation to auditory frequency mismatch," Hear Res., vol. 322, pp. 163-170 (Apr. 2015).

Stakhovskaya, O., et al., "Frequency Map for the Human Cochlear Spiral Ganglion: Implications for Cochlear Implants," Journal of the Association for Research in Otolaryngology (JARO), vol. 8, pp. 220-233 (2007).

Whitmal III, N.A., K. DeRoy, "Use of an adaptive-bandwidth protocol to measure importance functions for simulated cochlear implant frequency channels, "J Acoust Soc Am., vol. 131(2): pp. 1359-1370 (Feb. 2012).

Search Report and the Written Opinion in corresponding International Application No. PCT/IB2019/056066, mailed Dec. 13, 2019, 8 pages.

* cited by examiner

INDIVIDUALIZED ADAPTATION OF MEDICAL PROSTHESIS SETTINGS

BACKGROUND

Field of the Invention

The present invention generally relates to individualized adaptation of settings in medical prostheses.

Related Art

Medical prosthesis/devices having one or more implantable components, generally referred to herein as implantable medical prostheses, have provided a wide range of therapeutic benefits to recipients over recent decades. In particular, partially or fully-implantable medical prostheses such as auditory prostheses (e.g., bone conduction devices, mechanical stimulators, cochlear implants, etc.), implantable pacemakers, defibrillators, functional electrical stimulation devices, and other implantable medical devices, have been successful in performing lifesaving and/or lifestyle enhancement functions for a number of years.

The types of implantable medical prostheses and the ranges of functions performed thereby have increased over the years. For example, many implantable medical prostheses now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, the implantable medical prosthesis.

SUMMARY

In one aspect, a method is provided. The method comprises: determining an initial group of operational settings for a medical prosthesis associated with a recipient; determining a target group of operational settings for the medical prosthesis; determining a recipient-specific adaptation model for transitioning operation of the medical prosthesis from the initial group of operational settings to the target group of operational settings; programming the medical prosthesis to operate in accordance with the initial group of operational settings, with the target group of operational settings, and the recipient-specific adaptation model; and initiating, at the medical prosthesis, adaptation from operation with the initial group of operational settings to the target group of operational settings in accordance with the recipient-specific adaptation model.

In another aspect, a method is provided. The method comprises: receiving, at a medical prosthesis, a first group of operational settings and a second group of operational settings that are different from the first group of operational settings; operating the medical prosthesis using the first group of operational settings; and adapting operation of the medical prosthesis from the operation in accordance with the first group of operation settings to operation in accordance the second group of operational settings, wherein the adaptation occurs over a period of time and in a series of incremental steps that are set based on recipient-specific information associated with a recipient of the medical prosthesis.

In another aspect, an auditory prosthesis is provided. The auditory prosthesis comprises: one or more sound input devices; a plurality of electrodes implanted in a cochlea of a recipient; and one or more processors configured to: use an initial frequency encoding map to encode sound signals received at the one or more sound input devices into stimulation signals for delivery to the recipient, and adapt, over a period of time, to use of a target frequency encoding map to encode sound signals received at the one or more sound input devices into stimulation signals for delivery to the recipient, wherein the target frequency encoding map is customized based on one or more attributes of the recipient.

In another aspect, an auditory prosthesis is provided. The auditory prosthesis comprises: one or more sound input devices; and one or more processors configured to: receive a first group of operational settings and a second group of operational settings that are different from the first group of operational settings, use the first group of operational settings to convert sound signals received at the one or more sound input devices into stimulation signals for delivery to the recipient, and adapt to use of the second group of operational settings for conversion of sound signals received at the one or more sound input devices into stimulation signals for delivery to the recipient, wherein the adaptation to use of the second group of operational settings occurs over a period of time and in a series of incremental steps that are set based on recipient-specific information associated with a recipient of the auditory prosthesis.

BRIEF DESCRIPTION OF THE DRAWINGS

Embodiments of the present invention are described herein in conjunction with the accompanying drawings, in which.

DETAILED DESCRIPTION

Presented herein are techniques for adapting/transitioning operation of a medical prosthesis, such as an auditory prosthesis, from a first or initial group of settings to a second or target group of settings. The adaptation in the operation of the medical prosthesis from the first group of settings to the second group of settings occurs over a period of time and in a series of individualized (recipient-specific) incremental steps. That is, the adaptation process occurs in incremental steps that are set based on attributes/characteristics of the recipient of the specific medical prosthesis so that the adaptation is made as unobtrusive to the recipient as possible.

Merely for ease of description, the techniques presented herein are primarily described herein with reference to one illustrative medical prosthesis, namely a cochlear implant. However, it is to be appreciated that the techniques presented herein may also be used with a variety of other medical prosthesis or medical devices that, while providing a wide range of therapeutic benefits to recipients, patients, or other users, may benefit from the techniques presented. For example, the techniques presented herein may be used with other auditory prostheses, including acoustic hearing aids, auditory brainstem stimulators, bone conduction devices, middle ear auditory prostheses, direct acoustic stimulators, bimodal auditory prosthesis, bilateral auditory prosthesis, etc. The techniques presented herein may also be used with other medical prostheses, such as visual prostheses (e.g., retinal prostheses), etc.

Figure 1A:
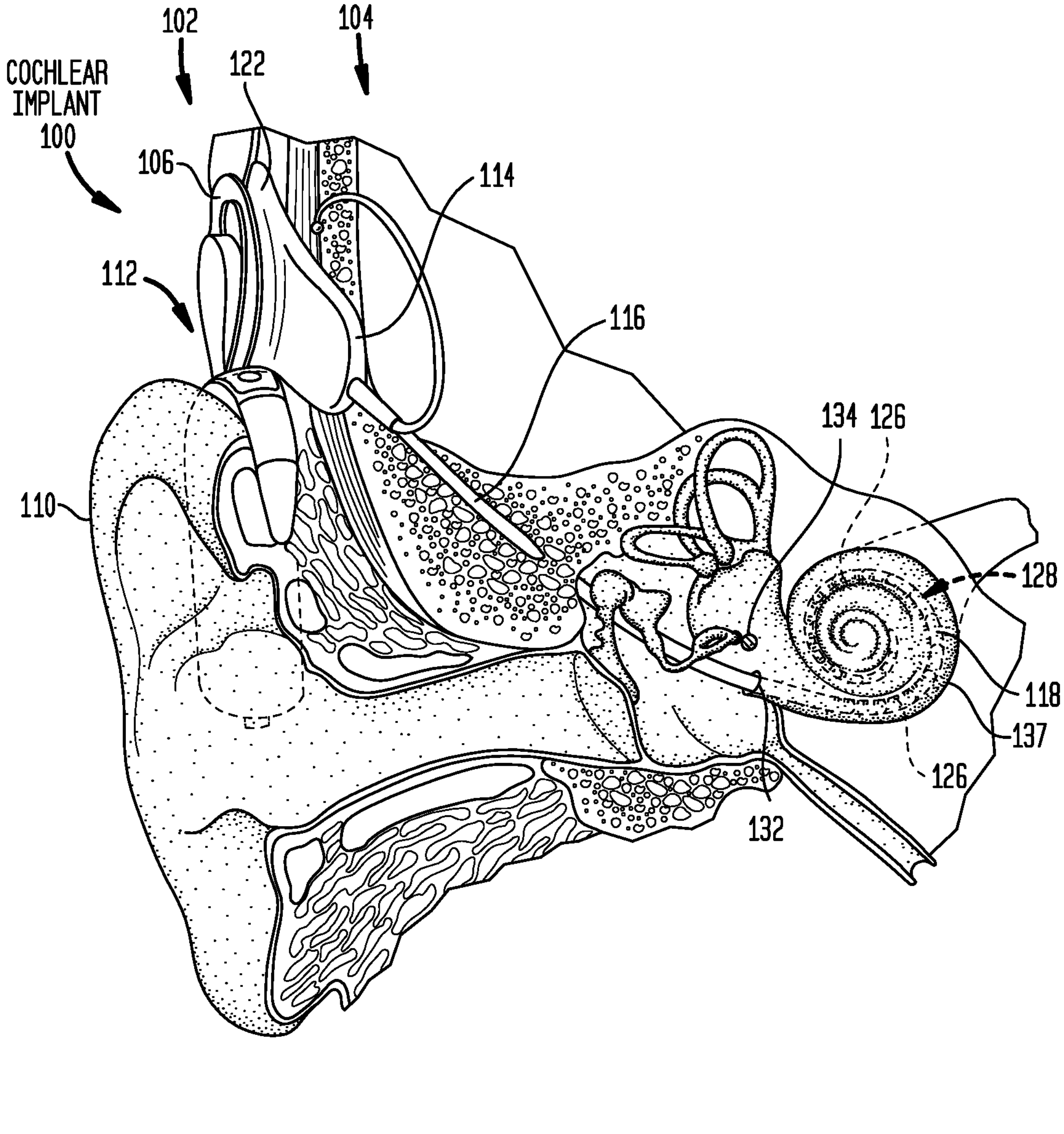
FIG. 1A is a schematic diagram illustrating a cochlear implant, in accordance with certain embodiments presented herein.
Figure 1B:
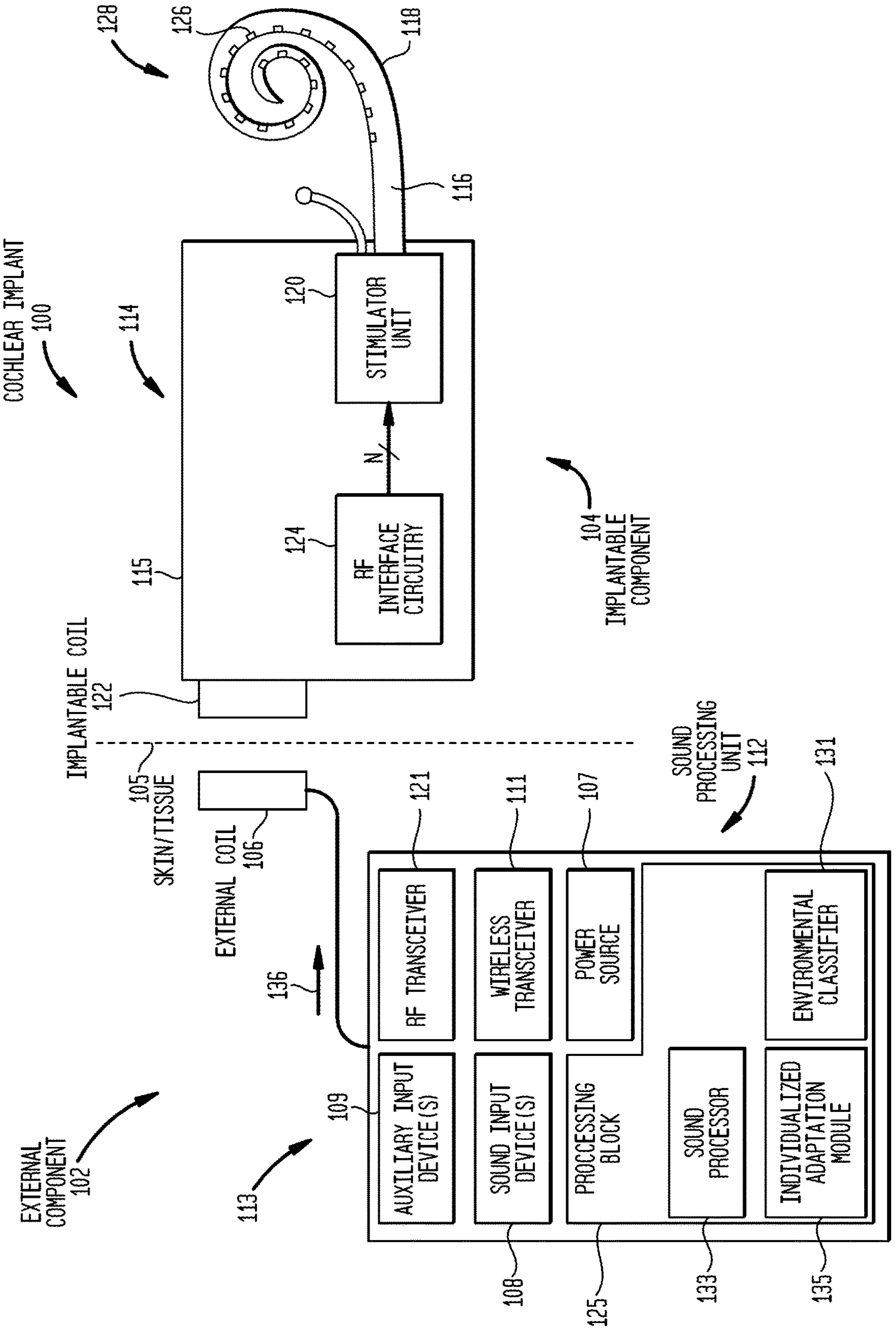
FIG. 1B is a block diagram of the cochlear implant of FIG. 1A.

FIG. 1A is a schematic diagram of an exemplary cochlear implant 100 configured to implement aspects of the techniques presented herein, while FIG. 1B is a block diagram of the cochlear implant 100. For ease of illustration, FIGS. 1A and 1B will be described together.

The cochlear implant 100 comprises an external component 102 and an internal/implantable component 104. The external component 102 is directly or indirectly attached to the body of the recipient and typically comprises an external coil 106 and, generally, a magnet (not shown in FIG. 1) fixed relative to the external coil 106. The external component 102 also comprises one or more input elements/devices 113 for receiving input signals at a sound processing unit 112. In this example, the one or more input devices 113 include sound input devices 108 (e.g., microphones positioned by auricle 110 of the recipient, telecoils, etc.) configured to capture/receive input signals, one or more auxiliary input devices 109 (e.g., audio ports, such as a Direct Audio Input (DAI), data ports, such as a Universal Serial Bus (USB) port, cable port, etc.), and a wireless transmitter/receiver (transceiver) 111, each located in, on, or near the sound processing unit 112.

The sound processing unit 112 also includes, for example, at least one battery 107, a radio-frequency (RF) transceiver 121, and a processing block 125. The processing block 125 comprises a number of elements, including an environmental classifier 131, a sound processor 133, and an individualized adaptation module 135. Each of the environmental classifier 131, the sound processor 133, and the individualized adaptation module 135 may be formed by one or more processors (e.g., one or more Digital Signal Processors (DSPs), one or more uC cores, etc.), firmware, software, etc. arranged to perform operations described herein. That is, the environmental classifier 131, the sound processor 133, and the individualized adaptation module 135 may each be implemented as firmware elements, partially or fully implemented with digital logic gates in one or more application-specific integrated circuits (ASICs), partially or fully in software, etc.

As described further below, the individualized adaptation module 135 is programmed to control the adaptation or transition operation of the cochlear implant 100 from operation in accordance with a first or initial group of setting to operation in accordance with a final or target group of settings. The individualized adaptation module 135 controls the adaptation in a recipient-specific (e.g., individualized) manner, meaning that the adaptation is tailored to the specific recipient of the cochlear implant (e.g., based on recipient-specific information. This recipient-specific information may include specific personal attributes of the recipient (e.g., current age, age of onset of hearing loss, duration of hearing loss, type of hearing loss, auditory sensitivity, attitude towards and/or expectations of the therapy, neurocognitive function and processing, IQ, brain plasticity, etc.), specific operation of the cochlear implant for the recipient (e.g., sound processing strategy, sound environment, cognitive load, etc.), sound optimization preferences of the recipient (e.g., optimization for speech perception, optimization for music perception), etc.

For ease of description, the techniques presented herein are primary described with reference to the adaptation of one specific group of settings, namely a recipient's "frequency encoding map" or simply the recipient's "map." As described further below, the recipient's "frequency encoding map" (map) is used by the auditory prosthesis to encode sound signals into stimulation signals. A recipient's map includes the recipient's "frequency-to-place assignment," which is an assignment of specific electrodes 126 for use in delivering stimulation signals representing specific acoustic frequencies. However, it is to be appreciated that the techniques presented herein may be used to transition cochlear implant 100 or another auditory prosthesis between other types of setting groups. For example, the techniques presented herein could be used to transition cochlear implant 100 from a current sound processing algorithm to a new sound algorithm.

Returning to the example embodiment of FIGS. 1A and 1B, the implantable component 104 comprises an implant body (main module) 114, a lead region 116, and an intracochlear stimulating assembly 118, all configured to be implanted under the skin/tissue (tissue) 105 of the recipient. The implant body 114 generally comprises a hermetically-sealed housing 115 in which RF interface circuitry 124 and a stimulator unit 120 are disposed. The implant body 114 also includes an internal/implantable coil 122 that is generally external to the housing 115, but which is connected to the RF interface circuitry 124 via a hermetic feedthrough (not shown in FIG. 1B).

As noted, stimulating assembly 118 is configured to be at least partially implanted in the recipient's cochlea 137. Stimulating assembly 118 includes a plurality of longitudinally spaced intra-cochlear electrical stimulating contacts (electrodes) 126 that collectively form a contact or electrode array 128 for delivery of electrical stimulation (current) to the recipient's cochlea. Stimulating assembly 118 extends through an opening in the recipient's cochlea (e.g., cochleostomy, the round window, etc.) and has a proximal end connected to stimulator unit 120 via lead region 116 and a hermetic feedthrough (not shown in FIG. 1B). Lead region 116 includes a plurality of conductors (wires) that electrically couple the electrodes 126 to the stimulator unit 120.

As noted, the cochlear implant 100 includes the external coil 106 and the implantable coil 122. The coils 106 and 122 are typically wire antenna coils each comprised of multiple turns of electrically insulated single-strand or multi-strand platinum or gold wire. Generally, a magnet is fixed relative to each of the external coil 106 and the implantable coil 122. The magnets fixed relative to the external coil 106 and the implantable coil 122 facilitate the operational alignment of the external coil with the implantable coil. This operational alignment of the coils 106 and 122 enables the external component 102 to transmit data, as well as possibly power, to the implantable component 104 via a closely-coupled wireless link formed between the external coil 106 with the implantable coil 122. In certain examples, the closely-coupled wireless link is a radio frequency (RF) link. However, various other types of energy transfer, such as infrared (IR), electromagnetic, capacitive and inductive transfer, may be used to transfer the power and/or data from an external component to an implantable component and, as such, FIG. 1B illustrates only one example arrangement.

As noted above, sound processing unit 112 includes the processing block 125. The processing block 125 is configured to convert input audio signals into stimulation control signals 136 for use in stimulating a first ear of a recipient (i.e., the processing block 125 is configured to perform sound processing on input audio signals received at the sound processing unit 112). Stated differently, the sound processor 133 (e.g., one or more processing elements implementing firmware, software, etc.) is configured to convert the captured input audio signals into stimulation control signals 136 that represent electrical stimulation for delivery to the recipient. The input audio signals that are processed and converted into stimulation control signals may be audio signals received via the sound input devices 108, signals received via the auxiliary input devices 109, and/or signals received via the wireless transceiver 111.

In the embodiment of FIG. 1B, the stimulation control signals 136 are provided to the RF transceiver 121, which transcutaneously transfers the stimulation control signals 136 (e.g., in an encoded manner) to the implantable component 104 via external coil 106 and implantable coil 122. That is, the stimulation control signals 136 are received at the RF interface circuitry 124 via implantable coil 122 and provided to the stimulator unit 120. The stimulator unit 120 is configured to utilize the stimulation control signals 136 to generate electrical stimulation signals (e.g., current signals) for delivery to the recipient's cochlea via one or more stimulating contacts 126. In this way, cochlear implant 100 electrically stimulates the recipient's auditory nerve cells, bypassing absent or defective hair cells that normally transduce acoustic vibrations into neural activity, in a manner that causes the recipient to perceive one or more components of the input audio signals.

Figure 2:
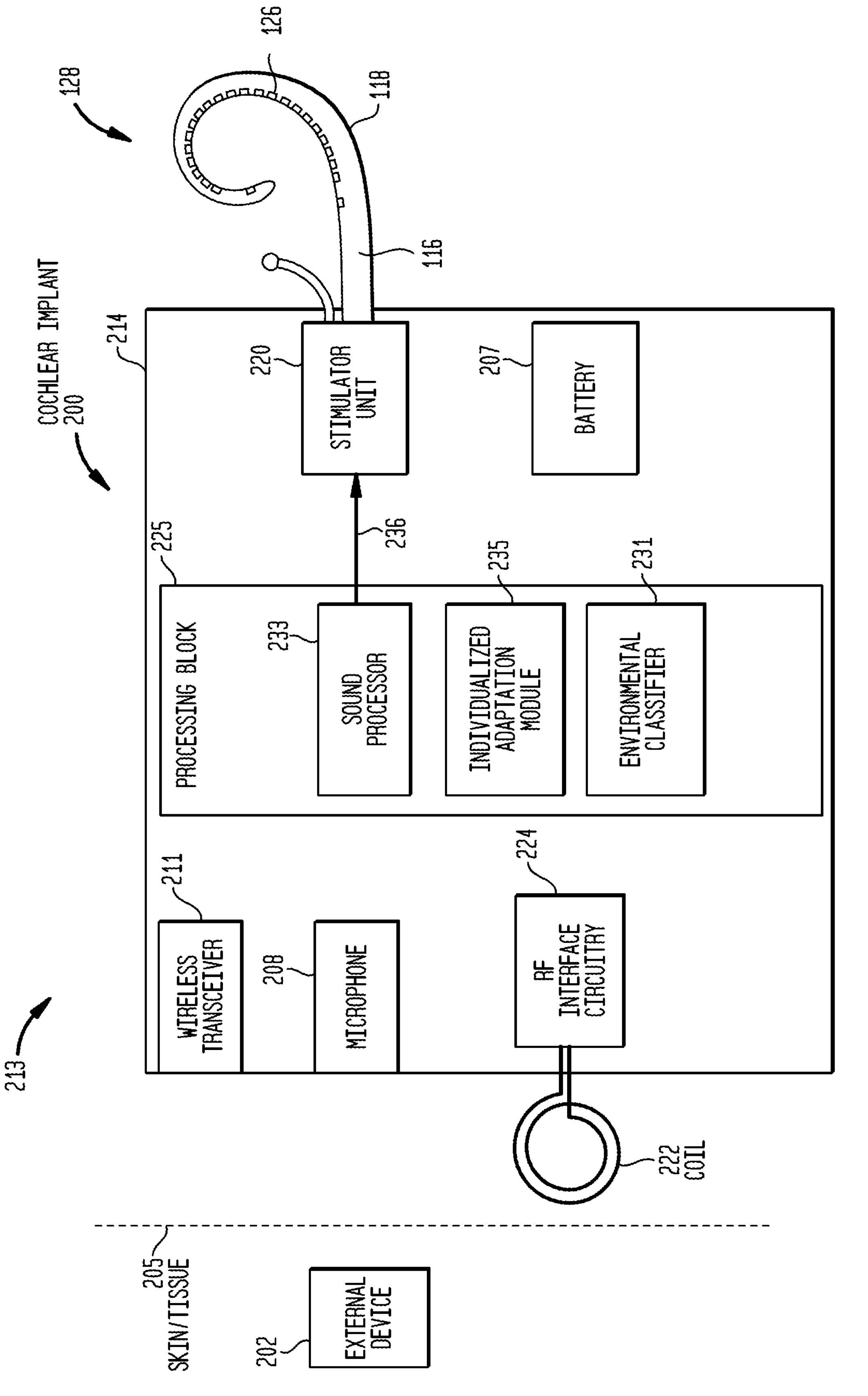
FIG. 2 is a block diagram of a totally implantable cochlear implant, in accordance with certain embodiments presented herein.

FIGS. 1A and 1B illustrate an arrangement in which the cochlear implant 100 includes an external component. However, it is to be appreciated that embodiments of the present invention may be implemented in cochlear implants having alternative arrangements. For example, FIG. 2 is a functional block diagram of an exemplary totally implantable cochlear implant 200 configured to implement embodiments of the present invention. Since the cochlear implant 200 is totally implantable, all components of cochlear implant 200 are configured to be implanted under skin/tissue 205 of a recipient. Because all components are implantable, cochlear implant 200 operates, for at least a finite period of time, without the need of an external device. An external device 202 can be used to, for example, charge an internal power source (battery) 207. External device 202 may be, for example, a dedicated charger or a conventional cochlear implant sound processor.

Cochlear implant 200 includes an implant body (main implantable component) 214, one or more input elements 213 for capturing/receiving input audio signals (e.g., one or more implantable microphones 208 and a wireless transceiver 211), an implantable coil 222, and an elongate intra-cochlear stimulating assembly 118 as described above with reference to FIGS. 1A and 1B. The microphone 208 and/or the implantable coil 222 may be positioned in, or electrically connected to, the implant body 214. The implant body 214 further comprises the battery 207, RF interface circuitry 224, a processing block 225, and a stimulator unit 220 (which is similar to stimulator unit 120 of FIGS. 1A and 1B). The processing block 225 may be similar to processing block 125 of FIGS. 1A and 1B, and includes environmental classifier 231, sound processor 233, and individualized adaptation module 235, which are similar to the environmental classifier 131, sound processor 133, the individualized adaptation module 135, respectively, described with reference to FIG. 1B.

In the embodiment of FIG. 2, the one or more implantable microphones 208 are configured to receive input audio signals. The processing block 225 is configured to convert received signals into stimulation control signals 236 for use in stimulating a first ear of a recipient. Stated differently, the sound processor 233 is configured to convert the input audio signals into stimulation control signals 236 that represent electrical stimulation for delivery to the recipient.

As noted above, FIGS. 1A and 1B illustrate an embodiment in which the external component 102 includes the processing block 125. As such, in the illustrative arrangement of FIGS. 1A and 1B, the stimulation control signals 136 are provided to the implanted stimulator unit 120 via the RF link between the external coil 106 and the internal coil 122. However, in the embodiment of FIG. 2 the processing block 225 is implanted in the recipient. As such, in the embodiment of FIG. 2, the stimulation control signals 236 do not traverse the RF link, but instead are provided directly to the stimulator unit 220. The stimulator unit 220 is configured to utilize the stimulation control signals 236 to generate electrical stimulation signals that are delivered to the recipient's cochlea via one or more stimulation channels.

As noted, the techniques presented herein may be implemented in a number of different types of auditory prostheses. However, for ease of description, further details of the techniques presented herein will generally be described with reference to cochlear implant 100 of FIGS. 1A-1B.

A recipient's cochlea is tonotopically mapped, that is, partitioned into regions each responsive to sound signals in a particular frequency range. In general, the basal region of the cochlea is responsive to higher frequency sounds, while the more apical regions of the cochlea are responsive to lower frequency sounds. The tonopotic nature of the cochlea is leveraged in cochlear implants such that specific acoustic frequencies are allocated to the electrodes of the stimulating assembly that are positioned close to the corresponding tonotopic region of the cochlea (i.e., the region of the cochlea that would naturally be stimulated in acoustic hearing by the acoustic frequency). That is, during fitting/programming of a cochlea implant, the electrodes of the electrode array are each assigned to stimulate the recipient with signals that represent specific acoustic frequencies and/or acoustic frequency ranges. This assignment of electrodes to frequencies is sometimes referred to herein as the recipient's "frequency-to-place assignment," which forms part of the recipient's "frequency map," sometimes referred to herein more simply as the recipient's "map." During operation, a cochlear implant sound processor performs an encoding step that uses the recipient's map to determine which electrodes should be used to deliver stimulation signals representing different frequency portions of the received sound signals.

However, following implantation of an electrode array into a recipient's cochlea, there may be a mismatch between the recipient's determined frequency-to-place assignment and the natural frequency map of the cochlea. As such, when cochlear implants are first activated, they often sound unnaturally high-pitched to the recipient. Additionally, an electrode array may only cover cochlear frequencies from 800 hertz (Hz) to 16 kilohertz (kHz). However, the sound processor may only send frequencies from 200 Hz to 8 kHz, since these are the most important speech frequencies. This results in a non-uniform frequency mismatch where electrodes positioned adjacent to certain tonotopic regions of the cochlea that do not necessarily deliver stimulation signals corresponding to the exact same frequency in the received sound signals. Moreover, the optimal allocation of audio bandwidth across the electrode array for conveying maximal speech information may not only result in a frequency-to-place shift (e.g., due to a relatively basal-ward position of the electrode array compared to the cochlear location of the most important speech frequencies), but may also result in frequency compression, expansion, or warping. An example of a typical non-uniform frequency mismatch is shown in FIGS. 3A and 3B.

Figure 3A:
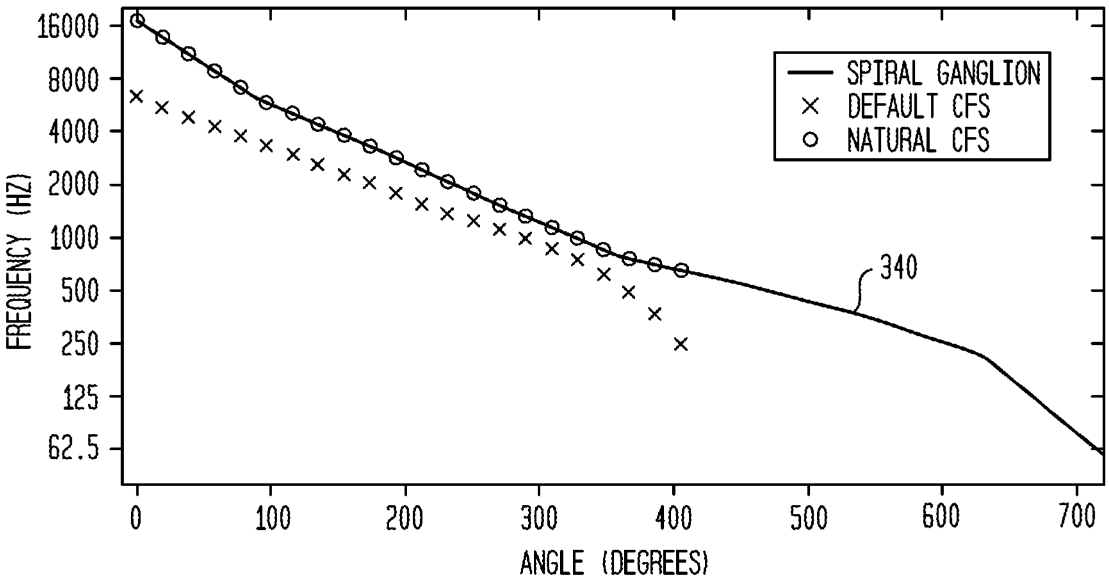
FIG. 3A is a graph illustrating natural center frequencies (CFs) of a recipient's spiral ganglion (cochlea nerve) cells and example angular location of twenty-two (22) electrodes of an electrode array implanted in the cochlea.
Figure 3B:
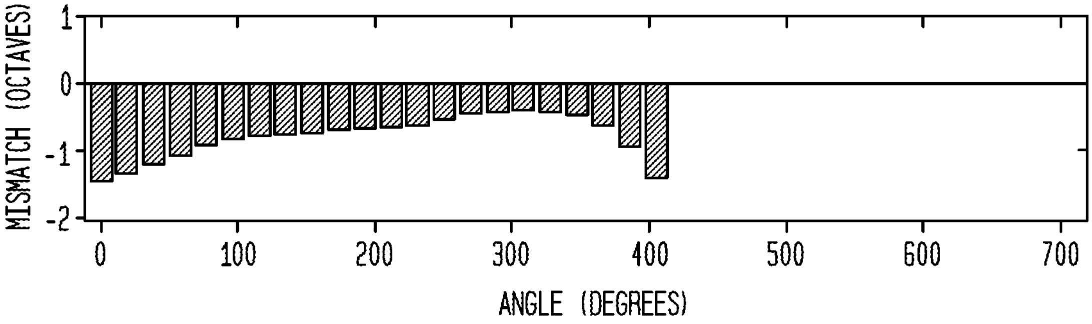
FIG. 3B is a graph illustrating the frequency mismatch, in octaves, between the natural center frequencies of the spiral ganglion cells and the default center frequencies of the twenty-two electrodes at the same electrode locations in FIG. 3A.

More specifically, line 340 in FIG. 3A represents the frequency response (i.e., tonotopic mapping) of the recipient's spiral ganglion (cochlea nerve) cells as a function of angle of rotation from the round window. Also shown in FIG. 3A are the natural center frequencies (CFs) of the spiral ganglion cells (represented using the circle shapes) and the example angular location of twenty-two (22) electrodes of an electrode array implanted in the cochlea and the corresponding default center frequencies (CFs) used in a typical sound processor (represented using the X shapes). FIG. 3B is a graph illustrating the frequency mismatch, in octaves, between the natural center frequencies of the spiral ganglion cells and the default center frequencies of twenty-two electrodes at the corresponding/same electrode locations (i.e., the frequency mismatch between the circle and X shapes in FIG. 3A).

These types of frequency mismatches may cause problems for cochlear implant recipients. For example, electric stimulation of the most basal electrodes (higher frequency areas) may initially be uncomfortable or especially annoying due to years of high-frequency auditory deprivation, as is common with progressive, age-related hearing losses in older adults.

In conventional arrangements, the expectation is for a recipient to simply "learn" the new/unnatural map (frequency-to-place assignment) over a period of time through training and auditory exposure. That is, the recipient is expected to learn to accept the frequency mismatches. However, this expectation detracts from the recipient's user experience as the sounds are unnatural (e.g., shifted from how a non-hearing impaired person perceives the same sounds) and some cochlear implant recipients may more readily "learn" to accept such frequency mismatches than other recipients. The frequency mismatches are especially problematic for those that have had previous acoustic hearing, or still retain some residual hearing (e.g., recipient's with electro-acoustic auditory prosthesis, residual hearing in the other ear as is the case with bimodal hearing devices, recipients with single-sides deafness (SSD), etc.). Unlike hearing aids, which can be returned if a recipient does not like the sound, cochlear implants and electro-acoustic auditory prosthesis are implanted and, accordingly, recipients are more likely to continue to use a cochlear implant even if the sound quality is poor.

As such presented herein are techniques that address these problems with conventional arrangements requiring recipient's to accept a new or unnatural map. More specifically, in order to maximize "naturalness" of sound at activation of a new (e.g., first) map, the recipient's cochlear implant is programmed with an "initial" or "first" map, which includes an initial frequency-to-place assignment that closely matches the placement of the electrodes and the natural frequency map of the cochlea. Additionally, lower stimulation (current) levels may be set for any basal electrodes that are perceived by the recipient as being too high pitched. In addition to the initial map, the cochlear implant is also programmed with "target" or "final" map, which includes a target frequency-to-place assignment. Whereas the initial frequency-to-place assignment that closely matches the placement of the electrodes and the natural frequency map of the cochlea, the target frequency-to-place assignment does not and, instead may be optimized based on sound preferences of the recipient. For example, the frequency-to-place assignment could be optimized for speech perception, optimized for music perception, or in some other manner.

In the techniques presented herein, at first activation the initial frequency-to-place assignment is used by the cochlear implant for encoding of sound signals. Over the course of a selected period of time (e.g., days, weeks, and/or months), the frequency-to-place assignment is slowly adapted, using a series of incremental steps, towards the target frequency-to-place assignment. In accordance with embodiments presented herein, the frequency-to-place assignment adaptation occurs in an individualized (i.e., recipient-specific) manner from the initial frequency-to-place assignment to the target frequency-to-place assignment. That is, the incremental steps used to transition from the initial frequency-to-place assignment to the target frequency-to-place assignment are set based on attributes/characteristics of the recipient of the specific auditory prosthesis. As a result, the adaptation is made as unobtrusive to the recipient as possible (e.g., so that the recipient does not notice the adaptive changes as the frequency-to-place assignment changes). By selecting an initial frequency-to-place assignment that closely matches the placement of the electrodes and the natural frequency map of the cochlea (i.e., naturally aligned boundaries optimized for natural sound quality and patient acceptance), the techniques presented herein provide a more immediate acceptance of electrical stimulation and hearing with the cochlear implant. However, by migrating the recipient to an optimized frequency-to-place assignment (e.g., optimized for maximal transfer of important speech information), the cochlear implant still achieves improved sound quality and, for example, optimal speech perception in the long term.

In accordance with embodiments presented herein, the target frequency-to-place assignment may be a customized frequency-to-place assignment optimized for the individual recipient. Also, for any high-frequency electrodes that were set to artificially low stimulation levels (below the normal loudness targets), the techniques also set target stimulation levels for eventual stimulation at the optimum loudness levels. Therefore, in accordance with the techniques presented herein, the adaptation may have multiple dimensions, including adaptation in the frequency-to-place assignment, adaptation in stimulation (current) levels, and adaptation in activated channels. As described further below, each of these different adaptation dimensions may be customized to the specific recipient (i.e., multiple individualized adaptation dimensions).

Figure 4:
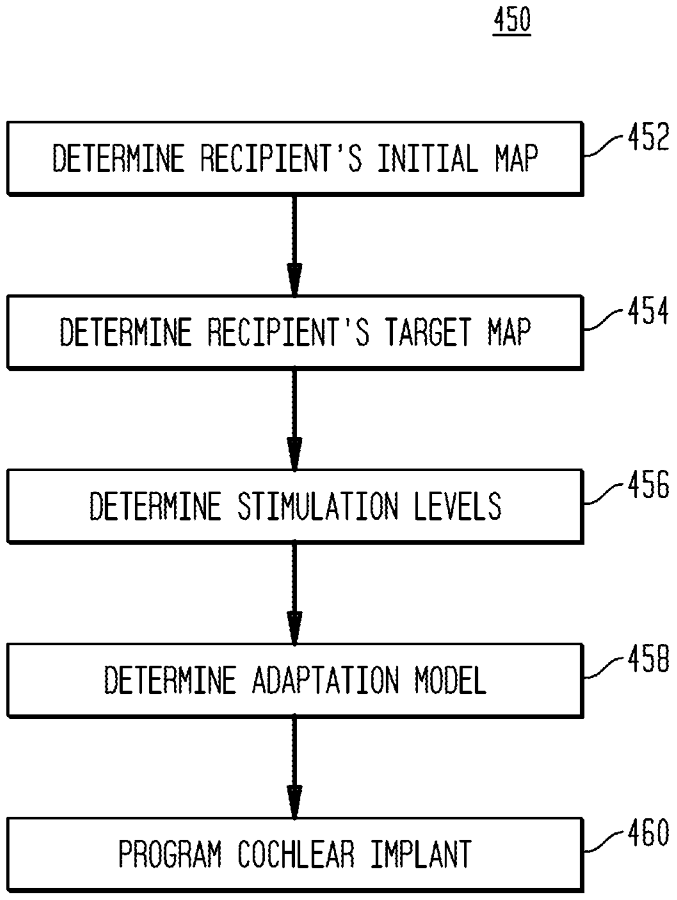
FIG. 4 is a flowchart of a method, in accordance with certain embodiments presented herein.

FIG. 4 is a flowchart of a method 450 in accordance with embodiments presented herein. For ease of description, method 450 will be described with reference to cochlear implant of FIGS. 1A and 1B. However, it is to be appreciated that method 450 may be executed with other types of auditory prostheses.

Method 450 begins at 452 where an "initial" map, including an initial frequency-to-place assignment, is determined for the recipient. The recipient's initial map may be determined in a number of different manners but is generally selected so that the initial frequency-to-place assignment closely matches the placement of the electrodes 126 and the natural frequency map of the cochlea 137.

For example, in certain arrangements a determined surgical insertion depth of the stimulating assembly 118, electrode dimensions, imaging (e.g., X-ray, computed tomography (CT), magnetic resonance imaging (MRI), etc.) may be used to determine the radial location of the electrodes 126 within the recipient's cochlea 137. In other examples, electrical measurements, subjective listening tests, matching to the other ear, data averaging, and/or other methods may be used to estimate the radial locations of the electrodes 126 within the recipient's cochlea 137. The radial locations of the electrodes 126 are analyzed relative to the tonotopic mapping of the recipient's cochlea 137 (i.e., the locations of the natural frequencies of the cochlea). The tonotopic mapping of the cochlea 137 may be determined in similar or other manners.

Based on the analysis of the radial locations of the electrodes 126 relative to the tonotopic mapping of the recipient's cochlea 137, the electrodes 126 are assigned/mapped to frequencies that correspond to the adjacent (i.e., most closely located) natural frequencies, resulting in the recipient's initial frequency-to-place assignment for inclusion in the recipient's initial map. Stated differently, electrodes 126 are assigned a center frequency that most closely matches a nearby (most closely located) natural frequency such that the recipient is stimulated with sounds matching the cochlear place of stimulation.

In certain examples, the recipient's initial map may omit low frequencies and/or high frequencies. For example, it may be beneficial to ensure that, at least in the initial map, the recipient is not stimulated at cochlear frequencies above an upper threshold frequency, such as above 8,000 Hz. Therefore, if there are basal electrodes located at cochlear regions above the upper threshold frequency (e.g., 8,000 Hz), then those electrodes are removed from the initial map. As a result, no stimulation will be provided to the recipient via any basal electrodes at cochlear locations above the upper threshold frequency. Alternatively, electrodes located at cochlear regions above the upper threshold frequency could only be stimulated using low current levels.

As noted, lower frequencies may also be omitted from the initial map. For example, it may be beneficial to ensure that, at least in the initial map, the recipient is not stimulated due to input sounds at frequencies below a lower threshold frequency, such as below 750 Hz. For example, if the most apical electrode is located at a cochlear region corresponding to 750 Hz, then sounds at frequencies much lower than this lower threshold of 750 Hz may not be delivered to the recipient with this initial map. In general, the goal of the initial map is to optimize for comfort, naturalness, and acceptance of the stimulation and resulting sound perception.

Returning to FIG. 4, at 454 a "target" or "second" map, including a target frequency-to-place assignment, is selected for the recipient. The target map can include a default frequency-to-electrode assignment for optimal speech perception or, in certain embodiments, can include an individualized (recipient-specific) frequency-to-electrode assignment.

As noted above, the recipient's initial frequency-to-place assignment may omit certain high frequency electrodes, use reduced current levels at certain high frequency electrodes, and/or omit certain lower frequency sounds. As such, the recipient's target map may include the addition of initially disabled electrodes (e.g., basal electrodes) located at cochlear regions having an associated natural frequency higher than the upper threshold frequency. The recipient's target map may also include increased current levels for any basal electrodes that were initially assigned low current levels in the initial map. Additionally, the recipient's target map may include assigning any low acoustic frequencies that were omitted in the initial map (e.g., due to being lower than the cochlear frequency of the most apical electrode) to, for example, the most apical electrode. In general, the goal of the target map is to optimize for high levels of speech understanding or another auditory target, such as music perception, and will likely deviate from the natural frequencies of the cochlea corresponding to the electrode locations.

As noted above, in certain embodiments the recipient's target map can include an individualized (recipient-specific) frequency-to-electrode assignment based on sound preferences of the recipient (e.g., a preference for speech perception, a preference for music perception, etc.). For example, in certain embodiments, a map for maximum transmission of speech information could be determined by measuring the information carrying capacity of each stimulation channel/electrode, taking into account the frequency band importance function of speech, and then evenly allocating speech-importance frequencies across the available channel/electrode capacity. Band importance functions, functions that describe the relative importance of different spectral regions for speech intelligibility, have been measured and defined for normal hearing and for simulations of cochlear implant hearing. A specific target map for optimal speech intelligibility might be one that evenly divides speech information across the electrode array according to one of these functions.

Furthermore, various measures for assessing the relative fitness of the channels/electrodes in average or individual ears can be used to estimate the relative information carrying capacity of the channels/electrodes and be used to distribute speech information more optimally. These measures may be histological, psychophysical, or evoked potentials. For example, the neural density of the spiral ganglion, as a function of angle, could show a general increase in neural density towards the apex of the cochlear. This suggests that more information could be distributed to the more apical electrodes. Example psychophysical tasks that could be used to compare the relative fitness of channels/electrodes include: detection threshold, number of discriminable loudness steps, modulation detection thresholds, interactions and discriminability with neighboring channels/electrodes, and multipulse integration. Example evoked potential measures that could be used to compare the relative fitness of channels/electrodes include: electrically-evoked compound action potential (ECAP) thresholds, slope of ECAP amplitude growth functions, ECAP amplitude at comfortable loudness, acoustic change complex, auditory steady-state responses, and other higher-order brain potentials. The following example, described with reference to FIGS. 5A-5C, demonstrates how this method could be applied to generate a target frequency map that is individualized (and optimized) for a recipient.

Figure 5A:
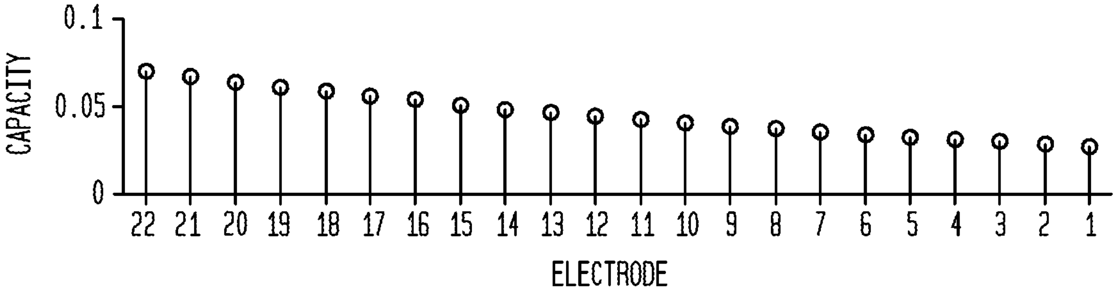
FIG. 5A is a graph illustrating the relative information capacity of each of twenty-two electrodes implanted in a cochlea of a recipient, in accordance with certain embodiments presented herein.
Figure 5B:
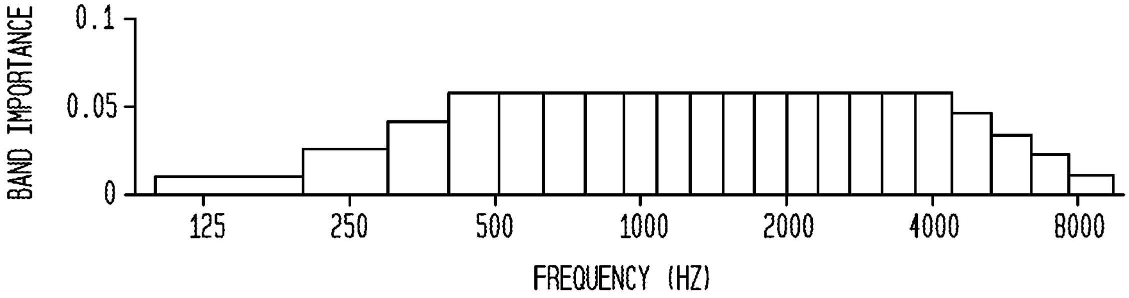
FIG. 5B is graph illustrating the relative importance of the cochlea frequency bands for speech understanding, in accordance with certain embodiments presented herein.
Figure 5C:
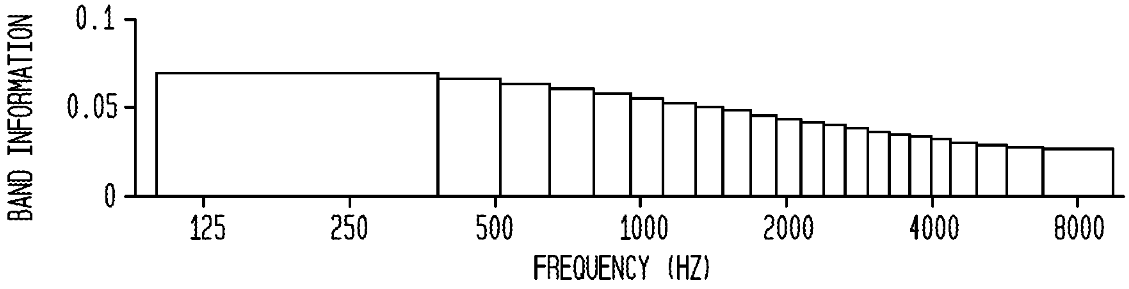
FIG. 5C is graph illustrating optimized frequency boundaries for the twenty-two electrodes of FIG. 5A such that speech information in each band is proportional to the relative information capacity of each corresponding electrode, in accordance with certain embodiments presented herein.

First, the relative information capacity of each electrode was determined based on neural density measures, as shown in FIG. 5A. In FIG. 5A, electrode number 22 is the most apical and stimulates lower frequency neurons, while electrode number 1 is the most basal and stimulates high frequencies. Next, as shown in FIG. 5B, the Speech Intelligibility Index (SII, ANSI S3.5-1997) is used to find the band importance function for speech. Finally, as shown in FIG. 5C, optimized frequency boundaries for the 22 electrodes are determined such that the speech information in each band is proportional to the relative information capacity of each corresponding electrode. In this example, since the low-frequency electrodes have higher information capacity, these electrodes get more bandwidth and speech information assigned to them, when compared to the high-frequency electrodes. In FIG. 5C, the amount of putative speech information, based on the SII band importance function, matches the capacity of each corresponding electrode.

Returning to FIG. 4, at 456 stimulation (current) levels, namely the recipient's threshold and comfort levels, for the recipient's initial and target maps are determined. The recipient's threshold levels are the minimum stimulation levels required to elicit auditory responses, whether perceptual, neural, or an auditory reflex. The recipient's comfort levels are the maximum stimulation levels at which auditory responses become uncomfortably loud.

The threshold and comfort levels may be determined based on individualized measurements or determined based on estimates from population data. The threshold and comfort levels are used in the cochlear implant 100 to map input acoustic sound pressure or energy to output stimulation levels at the electrodes 126 (e.g., from dB SPL to electric charge for each phase of a biphasic pulse train). As noted above, the stimulation levels selected for the initial map may be lower than those selected for the target map, especially for basal electrodes that are at high cochlear frequencies and/or that produce an uncomfortably high-frequency percept to the recipient.

At 458, the adaptation model (i.e., the set of rules/directives for adapting/transitioning from the initial group of settings to the target group of settings) is determined. That is, as used herein, the adaptation model includes all of the rules, regulations, directives, and other information for the incremental steps (or information for determination of the incremental steps) as to how the cochlear implant changes its operation from accordance with the first group of settings (e.g., the initial map) to the second group of settings (e.g., target map). As described elsewhere herein, the incremental adaptation steps may occur once per day and as frequently as once per minute of usage. Frequency steps may follow a cochleotopic, bark scale, or logarithmic trajectory.

As noted above, in accordance with embodiments presented herein, the adaptation model is individualized for the specific recipient of cochlear implant 100 (i.e., based on recipient-specific information). For example, after activation of the cochlear implant with the initial map, the adaptation model dictates that the automatic changes in frequency-to-place assignment towards that of the target map occur very slowly at the outset. The average rate of adaptation (e.g., how quickly the frequency-to-place assignment changes) can initially be set based on, for example, a recipient-specific attribute such as the estimated brain plasticity of the recipient. Brain plasticity can be estimated based on the recipient's age, duration of deafness, cognitive measures, and/or other factors expected to correlate with brain plasticity. For example, an 80-year old would be expected to have lower brain plasticity than a 30-year old, and thus a slower adaptation rate would be used with the older recipient.

The duration of adaptation will depend on the rate of adaptation and the magnitude of the difference between the frequency-to-place assignments of the initial and target maps. For example, with an adaptation rate of 0.2 octaves per week, and an average frequency difference of 1.2 octaves between the frequency-to-place assignments of the initial and target maps, the adaptation process would take approximately 6 weeks. Since the frequency difference will often vary across electrodes, for example as shown above in FIGS. 3A and 3B, the adaptation rate could vary for each electrode individually so that each electrode takes the same amount of time to reach the target frequency and levels.

The adaptation rate may also vary across the adaptation process. For example, the incremental changes may occur less frequently at the beginning of the adaptation time period, but the frequency of changes may increase as the recipient approaches the target. These different rates may be determined at the outset, determined dynamically during the process, etc. For example, in some embodiments subjective feedback (i.e., recipient responds to listening tests) and/or objective feedback (e.g., neural responses) from the recipient may be gathered at different points during the adaptation process and used to adjust the adaptation rate and/or other aspects of the adaptation model.

The actual course (e.g., rate) of adaptation may also vary based on environmental or situational factors of the recipient and, as such, can be varied during the adaptation process. These variations in the adaptation process could be automatic or via manual intervention. For example, the adaptation could be set to only occur over time periods that contain significant quantities of speech or another sound class (e.g., music) for which the target map is optimized, upon the detection conversational turns, etc. The adaptation could also pause during periods of silence or in other sound classes (e.g., noise). Another modification to the adaptation process could be based on multiple assessments of sound quality or satisfaction. For example, a daily assessment of sound quality could be made via a mobile device. If the recipient reports a deterioration in sound quality, then adaptation rate would be slowed and perhaps reversed until sound quality is restored. In other words, the rate of change of settings may not be uniform and could change dynamically on a day to day basis based on the environments, conversational, turns, etc.

As noted above, the transition from an initial to target frequency-to-place assignment (i.e., the adaptation in the frequency-to-place assignment) is one possible dimension of the adaptation process in accordance with embodiments presented. In further embodiments, the adaptation process may have other dimensions, including adaptation in current levels and adaptation in activated channels. Each of these different adaptation dimensions may be customized for the specific recipient.

More specifically, certain electrodes that are activated and used in the initial map may have a lower than normal initial current level in the initial map, but a higher target current level in the target map. For these electrodes, the stimulation (current) level would increase in steps that follow linear clinical units, which are typically logarithmic changes in current level or charge. Similar to the above, the rate of change in the current levels during the adaptation process may depend on recipient-specific information and may vary through the adaptation process. The rate of change in the current levels could also vary based on environmental or situational factors of the recipient.

For electrodes that are inactive in the initial map, but are active in the target map, the electrode will be activated upon a specific frequency-to-electrode shift. Once an electrode is activated due to the corresponding specific frequency-to-electrode shift, the electrode starts with no dynamic range at a recipient-specific threshold current level (i.e., the lowest current level at which a hearing percept is evoked) and is adapted to the full dynamic range of the target map over the remaining duration of the adaptation. That is, as electrodes are first activated during the adaptation process, the electrode is initially stimulated at a low current level (the recipient's threshold level). The current level associated with that electrode is adapted (increased) to a final (higher) level over the remainder of the adaptation process. Alternatively, once an electrode is activated due to the corresponding specific frequency-to-electrode shift, the electrode starts with both threshold and comfort levels at or below the recipient-specific perceptual threshold, with threshold level much lower than perceivable, and the full dynamic range is slowly shifted by adapting both threshold and comfort level towards the target levels.

Again returning to FIG. 4, at 460 the cochlear implant is programmed with all of the information for the adaptation process. That is, the cochlear implant is programmed with the initial map, the target map, and the adaptation model, including any rules that could warrant intervention by a clinician or other user.

FIG. 4 has generally been described with an example scenario in which the techniques presented herein are used to transition a cochlear implant 100 from an initial map to a target map. That is, in FIG. 4, the "initial" map is generally the very first map that a recipient's cochlear implant employs, and the "target" map is the first optimized map. However, it is to be appreciated that the techniques presented herein may be used in other scenarios, such as scenarios in which a recipient already has a cochlear implant and is fully accustomed to listening with a current frequency-to-place assignment. In such an example, a clinician may decide to migrate the recipient to an updated frequency-to-place assignment and may use the techniques presented herein to reach the target map over a period of time and in a manner that is specifically individualized for the recipient. In such scenarios, the "initial" map is the recipient's current map and "target" map is the updated frequency-to-place assignment. Such a scenario may occur, for example, in the case of new technology that expands the acoustic bandwidth of the cochlear implant.

In a similar manner, a recipient could be transitioned from a current sound processing algorithm to a new or updated sound algorithm using the techniques presented herein. In such examples, the adaptation may have adaptation dimensions other than a frequency-to-place assignment, current levels, and/or activated channels. For example, a recipient could be transitioned from the Advanced Combination Encoder (ACE) sound processing algorithm, which by default stimulates at 900 pulses per second on each channel, to the Fundamental Asynchronous Stimulus Timing (FAST) sound processing algorithm, which uses lower and variable pulse rates. The ACE strategy samples the temporal envelope of each channel with fixed rate pulses, whereas the FAST strategy only stimulates once per each temporal envelope cycle, typically at the envelope peak. In such examples, the transition could be achieved by taking multiple intermediate steps from ACE to FAST by, for example, dropping a certain proportion of pulses within each temporal envelope cycle (e.g., first just a small proportion and later a larger proportion) until a single pulse at each envelope peak is reached. Yet another example would be transitioning from a higher fixed rate to a lower fixed rate within the ACE sound processing algorithm, such as from 900 pulses per second to 500 pulses per second, with any associated changes in stimulation current levels. Such changes are often desirable to lower the power consumption of the device, but it can be difficult for the patient to make large and sudden changes without the adaptation process of this invention.

As noted, FIG. 4 has also generally been described with an example scenario in which the techniques presented herein are used to transition a cochlear implant recipient to his/her first optimized map. However, it is to be appreciated that the techniques presented herein may also be used with other types of auditory prostheses. For example, another use of the techniques presented herein would be to modify operation of an electro-acoustic auditory prosthesis implanted in a recipient with residual hearing in the lower frequencies. An electro-acoustic auditory prosthesis uses a combination of electrical stimulation and acoustic stimulation, where the electrical stimulation is used to stimulate the high frequency regions of the cochlea and acoustic stimulation is used to stimulate the lower frequency regions of the cochlea. The techniques presented herein could be used to modify operation of such an electro-acoustic auditory prosthesis by, for example, slowly switching on the cochlear implant, slowing activating additional cochlear implant channels, and/or slowly reducing the acoustic gain of upper frequencies, such as above 500 Hz in the acoustic component (e.g., migrate from standard hearing aid fitting to an electro-acoustic fitting that is optimized for combined electric-acoustic stimulation with little overlap in frequencies).

Figure 6:
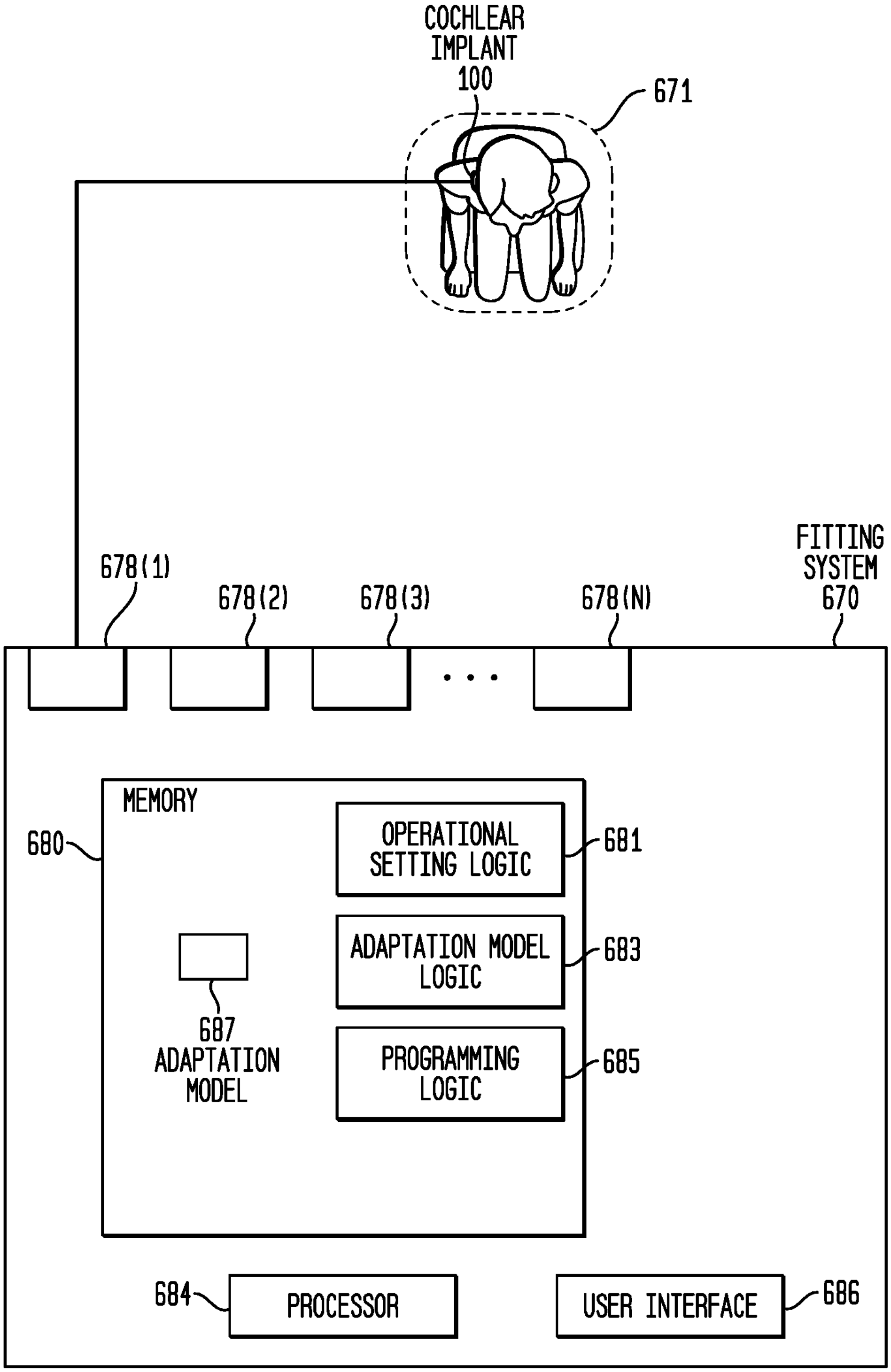
FIG. 6 is a block diagram of a system configured to execute techniques in accordance with certain embodiments presented herein.

FIG. 6 is block diagram illustrating an example computing device 670 (e.g., fitting system, computer, mobile computing device, etc.) configured to execute the techniques presented herein. Computing device 670 comprises a plurality of interfaces/ports 678(1)-678(N), a memory 680, a processor 684, and a user interface 686. The interfaces 678(1)-678(N) may comprise, for example, any combination of network ports (e.g., Ethernet ports), wireless network interfaces, Universal Serial Bus (USB) ports, Institute of Electrical and Electronics Engineers (IEEE) 1394 interfaces, PS/2 ports, etc. In the example of FIG. 6, interface 678(1) is connected to cochlear implant 100 having components implanted in a recipient 671. Interface 678(1) may be directly connected to the cochlear implant 100 or connected to an external device that is communication with the cochlear implant. Interface 678(1) may be configured to communicate with cochlear implant 100 via a wired or wireless connection (e.g., telemetry, Bluetooth, etc.).

The user interface 686 includes one or more output devices, such as a liquid crystal display (LCD) and a speaker, for presentation of visual or audible information to a clinician, audiologist, or other user. The user interface 686 may also comprise one or more input devices that include, for example, a keypad, keyboard, mouse, touchscreen, etc.

The memory 680 comprises operational setting logic 681 that may be executed to generate/determine an initial group of settings for the cochlear implant 100 and the target group of settings for the cochlear implant 100. The memory 680 also comprises adaptation model logic 683 that may be executed to generate/determine a recipient-specific adaptation model 687 (i.e., individualized set of adaptation rules) for adaptation of operation of the cochlear implant 100 from the initial group of settings to the target group of settings. The memory 680 may further include programming logic 685 that may be executed to configure/program the cochlear implant 100 with the initial group of settings, the target group of settings, and the adaptation model 687.

Memory 680 may comprise read only memory (ROM), random access memory (RAM), magnetic disk storage media devices, optical storage media devices, flash memory devices, electrical, optical, or other physical/tangible memory storage devices. The processor 684 is, for example, a microprocessor or microcontroller that executes instructions for the operational setting logic 681, the adaptation model logic 683, and the programming logic 685. Thus, in general, the memory 680 may comprise one or more tangible (non-transitory) computer readable storage media (e.g., a memory device) encoded with software comprising computer executable instructions and when the software is executed (by the processor 684) it is operable to perform the techniques described herein.

Figure 7:
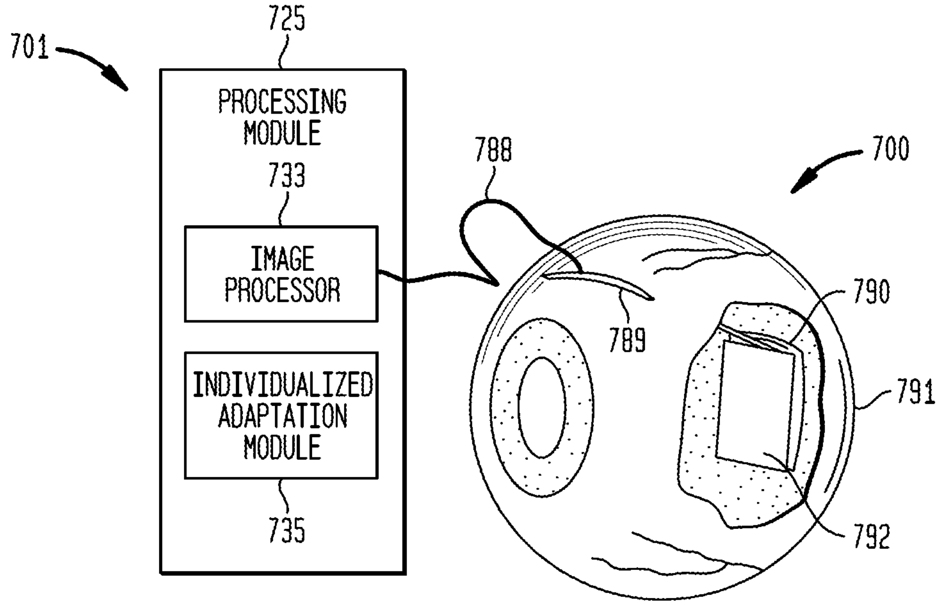
FIG. 7 is a schematic diagram illustrating a retinal prosthesis, in accordance with certain embodiments presented herein.

The techniques presented herein have generally been described above with reference to one example medical prosthesis, namely a cochlear implant. However, as noted above, the techniques presented herein may also be implemented in other types of medical prostheses. FIG. 7 is a schematic diagram illustrating an alternative medical prosthesis, namely a retinal prosthesis 700, configured to implement the techniques presented herein.

As shown, the retinal prosthesis 700 comprises a processing block/module 725 and a retinal prosthesis sensor-stimulator 790 is positioned proximate the retina 791 of a recipient. In an exemplary embodiment, sensory inputs (e.g., photons entering the eye) are absorbed by a microelectronic array of the sensor-stimulator 790 that is hybridized to a glass piece 792 including, for example, an embedded array of microwires. The glass can have a curved surface that conforms to the inner radius of the retina. The sensor-stimulator 790 can include a microelectronic imaging device that can be made of thin silicon containing integrated circuitry that convert the incident photons to an electronic charge.

The processing module 725 includes an image processor 723 that is in signal communication with the sensor-stimulator 790 via, for example, a lead 788 which extends through surgical incision 789 formed in the eye wall. In other embodiments, processing module 725 may be in wireless communication with the sensor-stimulator 790. The image processor 723 processes the input into the sensor-stimulator 790, and provides control signals back to the sensor-stimulator 790 so the device can provide an output to the optic nerve. That said, in an alternate embodiment, the processing is executed by a component proximate to, or integrated with, the sensor-stimulator 790. The electric charge resulting from the conversion of the incident photons is converted to a proportional amount of electronic current which is input to a nearby retinal cell layer. The cells fire and a signal is sent to the optic nerve, thus inducing a sight perception.

The processing module 725 may be implanted in the recipient or may be part of an external device, such as a Behind-The-Ear (BTE) unit, a pair of eyeglasses, etc. The retinal prosthesis 700 can also include an external light/image capture device (e.g., located in/on a BTE device or a pair of glasses, etc.), while, as noted above, in some embodiments, the sensor-stimulator 790 captures light/images, which sensor-stimulator is implanted in the recipient.

In the interests of compact disclosure, any disclosure herein of a microphone or sound capture device corresponds to an analogous disclosure of a light/image capture device, such as a charge-coupled device. Corollary to this is that any disclosure herein of a stimulator unit which generates electrical stimulation signals or otherwise imparts energy to tissue to evoke a hearing percept corresponds to an analogous disclosure of a stimulator device for a retinal prosthesis. Any disclosure herein of a sound processor or processing of captured sounds or the like corresponds to an analogous disclosure of a light processor/image processor that has analogous functionality for a retinal prosthesis, and the processing of captured images in an analogous manner. Indeed, any disclosure herein of a device for a hearing prosthesis corresponds to a disclosure of a device for a retinal prosthesis having analogous functionality for a retinal prosthesis. Any disclosure herein of fitting a hearing prosthesis corresponds to a disclosure of fitting a retinal prosthesis using analogous actions. Any disclosure herein of a method of using or operating or otherwise working with a hearing prosthesis herein corresponds to a disclosure of using or operating or otherwise working with a retinal prosthesis in an analogous manner.

Similar to the above embodiments, the retinal prosthesis 700 includes an individualized adaptation module 735 forming part of processing module 725. Similar to the individualized adaptation module 135 described above, the individualized adaptation module 735 is programmed to control the adaptation or transition operation of the retinal prosthesis 700 from operation in accordance with a first or initial group of setting to operation in accordance with a final or target group of settings. The individualized adaptation module 735 controls the adaptation in a recipient-specific (e.g., individualized) manner, meaning that the adaptation is specifically tailored to the specific recipient of the retinal prosthesis 700 (e.g., based on recipient-specific information). The individualized adaptation module 735 controls the adaptation in a recipient-specific (e.g., individualized) manner, meaning that the adaptation is specifically tailored to the specific recipient of the cochlear implant (e.g., based on recipient-specific information). This recipient-specific information may include specific attributes of the recipient (e.g., current age, age of onset of visual problem, brain plasticity, etc.) and/or specific operation of the retinal prosthesis 700 for the recipient.

Each of the image processor 733, and the individualized adaptation module 735 may be formed by one or more processors (e.g., one or more Digital Signal Processors (DSPs), one or more uC cores, etc.), firmware, software, etc. arranged to perform operations described herein. That is, the image processor 733, and the individualized adaptation module 735 may each be implemented as firmware elements, partially or fully implemented with digital logic gates in one or more application-specific integrated circuits (ASICs), partially or fully in software, etc.

Figure 8:
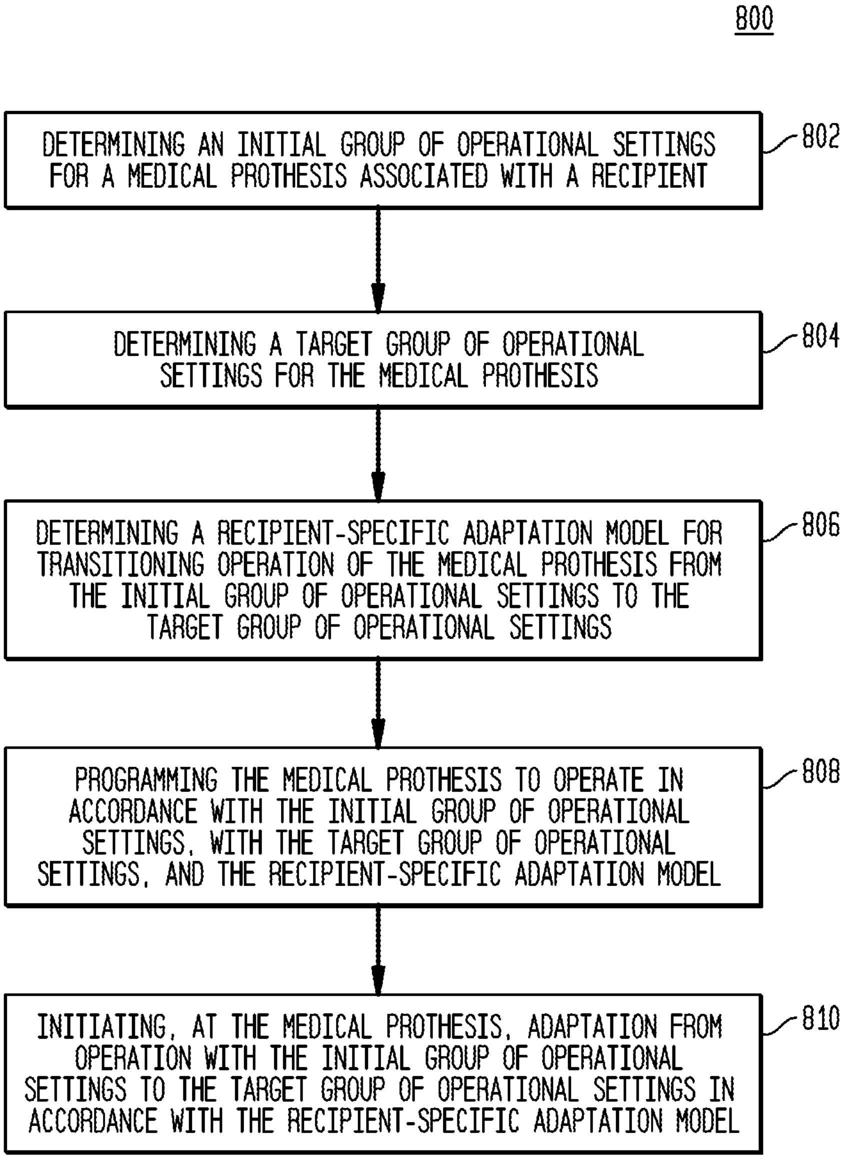
FIG. 8 is a flowchart of a method in accordance with embodiments presented herein.

FIG. 8 is a flowchart of a method 800 in accordance with embodiments presented herein. Method 800 begins at 802 where an initial group of operational settings for a medical prosthesis is determined. The medical prosthesis is associated with (e.g., implanted in or worn by a recipient). At 804, a target group of operational settings for the medical prosthesis is determined. At 806, a recipient-specific adaptation model for transitioning operation of the medical prosthesis from the initial group of operational settings to the target group of operational settings is determined. At 808, the medical prosthesis is programmed with the initial group of operational settings, with the target group of operational settings, and the recipient-specific adaptation model. At 810, adaptation from operation with the initial group of operational settings to the target group of operational settings in accordance with the recipient-specific adaptation model is initiated at the auditory prosthesis. In certain examples, the medical prosthesis may be an auditory prosthesis, such as an acoustic hearing aid, a prosthesis having a plurality of electrodes implanted in the recipient (e.g., a cochlear implant), etc.

Figure 9:
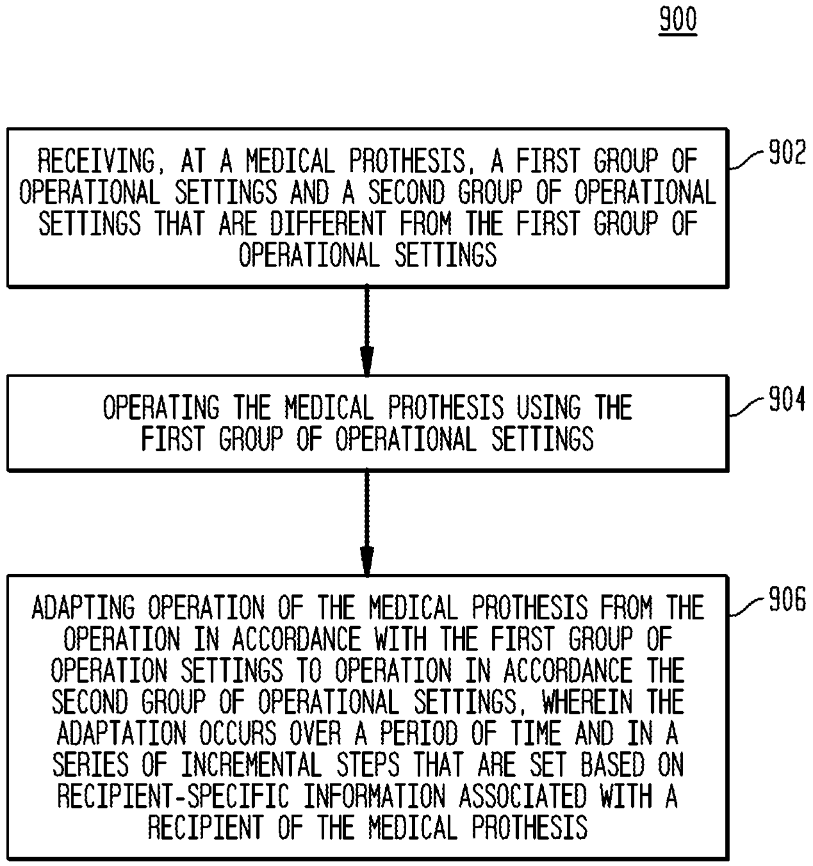
FIG. 9 is a flowchart of another method in accordance with embodiments presented herein.

FIG. 9 is a flowchart of a method 900 in accordance with embodiments presented herein. Method 900 begins at 902 where a medical prosthesis receives a first group of operational settings and a second group of operational settings that are different from the first group of operational settings. At 904, the medical prosthesis operates using the first group of operational settings. At 906, operation of the medical prosthesis is adapted from the operation in accordance with the first group of operation settings to operation in accordance the second group of operational settings. The adaptation occurs over a period of time and in a series of incremental steps that are set based on recipient-specific information associated with a recipient of the medical prosthesis. In certain examples, the medical prosthesis may be an auditory prosthesis, such as an acoustic hearing aid, a prosthesis having a plurality of electrodes implanted in the recipient (e.g., a cochlear implant), etc.

It is to be appreciated that the above described embodiments are not mutually exclusive and that the various embodiments can be combined in various manners and arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method comprising:

operating a hearing device associated with a recipient using an initial group of operational settings that include at least a first initial setting for use in determining stimulation signals to evoke perception of sound signals above a threshold frequency and at least a second initial setting for use in determining stimulation signals to evoke perception of sound signals below the threshold frequency, wherein operating the hearing device using the initial group of operational settings includes one of refraining from delivering stimulation signals to the recipient for sound signals above the threshold frequency according to the first initial setting, or delivering the stimulation signals with frequencies above the threshold frequency at a reduced stimulation level according to the first initial setting;

adapting operation of the hearing device from operating using the initial group of operational settings towards operating using a target group of operational settings for the hearing device in accordance with an adaptation model, wherein the target group of operational settings includes at least a first target setting for use in generating stimulation signals for sound signals above the threshold frequency and at least a second target setting for use in generating stimulation signals for sound signals below the threshold frequency; and after the adapting operation of the hearing device operating the hearing device using the target group of operational settings.

2. The method of claim 1, wherein the adaptation model defines a first series of individualized steps for transitioning operation of the hearing device from operation in accordance with the first initial setting to operation in accordance with the first target setting over a period of time, and wherein the adaptation model defines a second series of individualized steps for transitioning operation of the hearing device from operation in accordance with the second initial setting to operation in accordance with second target setting over the period of time.

3. The method of claim 2, wherein the first series of individualized steps for transitioning operation of the hearing device from operation in accordance with the first initial setting to operation in accordance with first target setting and the second series of individualized steps for transitioning operation of the hearing device from operation in accordance with the second initial setting to operation in accordance with the second target setting are set based on information associated with the recipient.

4. The method of claim 2, wherein the first series of individualized steps for transitioning operation of the hearing device from operation in accordance with the first initial setting to operation in accordance with first target setting are different from the second series of individualized steps for transitioning operation of the hearing device from operation in accordance with the second initial setting to operation in accordance with the second target setting.

5. The method of claim 1, wherein operating the hearing device using the target group of operational settings comprises:

delivering stimulation signals to the recipient for sound signals above the threshold frequency according to the first target setting.

6. The method of claim 1, wherein the hearing device comprises a plurality of electrodes implanted in a cochlea of the recipient, and wherein one or more electrodes located at a cochlear region associated with frequencies above the threshold frequency are disabled according to the first initial setting and are activated according to the first target setting.

7. The method of claim 6, wherein the adapting operation of the hearing device from operating using the initial group of operational settings to operating using the target group of operational settings in accordance with the adaptation model comprises:

activating the one or more electrodes located at the cochlear region associated with frequencies above the threshold frequency;

upon activating the one or more electrodes, delivering the stimulation signals for sounds above the threshold frequency to the recipient via the one or more electrodes at an initial stimulation current level; and dynamically increasing a current level of the stimulation signals for sounds above the threshold frequency towards a target current level over a period of time.

8. The method of claim 1, wherein operating the hearing device using an initial group of operational settings includes delivering the stimulation signals with frequencies above the threshold frequency at a reduced stimulation level, and comprises:

setting a stimulation level associated with frequencies above the threshold frequency at the reduced stimulation level according to the first initial setting.

9. The method of claim 8, wherein the reduced stimulation level according to the first initial setting is lower than a stimulation level associated with frequencies below the threshold frequency according to the second initial setting.

10. The method of claim 1, wherein the adapting operation of the hearing device from operating using the initial group of operational settings towards operating using a target group of operational settings in accordance with the adaptation model comprises:

transitioning the first initial setting towards the first target setting at an average rate that is determined based on information.

11. The method of claim 1, wherein the adapting operation of the hearing device from operating using the initial group of operational settings towards operating using a target group of operational settings in accordance with the adaptation model comprises:

dynamically changing a rate at which the first initial setting changes towards the first target setting.

12. A hearing device, comprising:

one or more first stimulation components configured to deliver first stimulation signals to a recipient to evoke perception of sound signals above a threshold frequency;

one or more second stimulation components configured to deliver second stimulation signals to a recipient to evoke perception of sound signals below the threshold frequency; and one or more processing components configured to:

operate the hearing device using an initial group of operational settings for the hearing device, the initial group of operational settings including at least a first initial setting for use in determining the first stimulation signals for sound signals above the threshold frequency and at least a second initial setting for use in determining the second stimulation signals for sound signals below the threshold frequency, wherein, when operating the hearing device using the initial group of operational settings, the one or more processing components are configured to:

refrain from delivering stimulation signals to the recipient for sound signals above the threshold frequency according to the first initial setting, or deliver the stimulation signals with frequencies above the threshold frequency at a reduced stimulation level according to the first initial setting;

adapt operation of the hearing device from operating using the initial group of operational settings towards operating using a target group of operational settings for the hearing device in accordance with an adaptation model for transitioning operation of the hearing device over a period of time and in a series of incremental steps that are set based on recipient-specific information associated with the recipient; and operate the hearing device using the target group of operational settings for the hearing device, including at least a first target setting for use in generating the first stimulation signals for sound signals above the threshold frequency and at least a second target setting for use in generating the second stimulation signals for sound signals below the threshold frequency.

13. The hearing device of claim 12, wherein the one or more processing components are configured to:

initiate adaptation of operation of the hearing device from operating using the initial group of operational settings towards operating using the target group of operational settings in accordance with the adaptation model.

14. The hearing device of claim 12, wherein the adaptation model defines a first series of individualized steps for transitioning operation of the hearing device from operation in accordance with the first initial setting to operation in accordance with the first target setting over a period of time, and wherein the adaptation model defines a second series of individualized steps for transitioning operation of the hearing device from operation in accordance with the second initial setting to operation in accordance with second target setting over the period of time.

15. The hearing device of claim 14, wherein the first series of individualized steps for transitioning operation of the hearing device from operation in accordance with the first initial setting to operation in accordance with first target setting and the second series of individualized steps for transitioning operation of the hearing device from operation in accordance with the second initial setting to operation in accordance with the second target setting are set based on information associated with the recipient.

16. The hearing device of claim 14, wherein the first series of individualized steps for transitioning operation of the hearing device from operation in accordance with the first initial setting to operation in accordance with first target setting are different from the second series of individualized steps for transitioning operation of the hearing device from operation in accordance with the second initial setting to operation in accordance with the second target setting.

17. The hearing device of claim 12, wherein the one or more first stimulation components comprises a plurality of electrodes implanted in a cochlea of the recipient, and wherein one or more electrodes located at a cochlea region associated with frequencies above the threshold frequency are disabled according to the first initial setting and are activated according to the first target setting.

18. The hearing device of claim 17, wherein the adapting operation of the hearing device from operating using the initial group of operational settings to operating using the target group of operational settings in accordance with the adaptation model comprises:

activating the one or more electrodes located at the cochlea region associated with frequencies above the threshold frequency;

upon activating the one or more electrodes, delivering the first stimulation signals for sounds above the threshold frequency to the recipient via the one or more electrodes at an initial stimulation current level; and dynamically increasing a current level of the stimulation signals for sounds above the threshold frequency towards a target current level over a period of time.

19. The hearing device of claim 12, wherein the processing components are configured to deliver the stimulation signals with frequencies above the threshold frequency at a reduced stimulation level, and the reduced stimulation level according to the first initial setting is lower than a stimulation level associated with frequencies below the threshold frequency according to the second initial setting.

20. The hearing device of claim 12, wherein, when adapting operation of the hearing device from operating using the initial group of operational settings towards operating using a target group of operational settings in accordance with the adaptation model, the one or more processing components are further configured to transition the first initial setting towards the first target setting at an average rate that is determined based on information.

* * * * *